United States Patent
Okuyama

(10) Patent No.: US 9,568,440 B2
(45) Date of Patent: Feb. 14, 2017

(54) FILTER INSPECTION METHOD AND APPARATUS

(75) Inventor: Tetsuya Okuyama, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 617 days.

(21) Appl. No.: 13/611,021

(22) Filed: Sep. 12, 2012

(65) Prior Publication Data

US 2013/0002853 A1   Jan. 3, 2013

Related U.S. Application Data

(63) Continuation of application No. PCT/JP2010/055100, filed on Mar. 24, 2010.

(51) Int. Cl.
| | |
|---|---|
| *G06K 9/00* | (2006.01) |
| *H04N 7/18* | (2006.01) |
| *G01N 21/952* | (2006.01) |
| *A24C 5/34* | (2006.01) |
| *A24D 3/02* | (2006.01) |
| *G01B 11/24* | (2006.01) |
| *G01N 21/88* | (2006.01) |
| *G06T 7/00* | (2006.01) |

(52) U.S. Cl.
CPC ........... *G01N 21/952* (2013.01); *A24C 5/3412* (2013.01); *A24D 3/0295* (2013.01); *G01B 11/2408* (2013.01); *G01N 21/8806* (2013.01); *G06T 7/001* (2013.01); *H04N 7/183* (2013.01)

(58) Field of Classification Search
CPC .. G01N 21/952; G01N 21/8806; H04N 7/183; G06T 7/001; A24C 5/3412; A24D 3/0295
USPC .............................. 348/86, 92; 382/141, 143
See application file for complete search history.

(56) References Cited

U.S. PATENT DOCUMENTS

| | | | |
|---|---|---|---|
| 4,502,261 A * | 3/1985 | Zullo | 53/54 |
| 5,588,068 A | 12/1996 | Longest et al. | |
| 6,384,359 B1 | 5/2002 | Belcastro et al. | |
| 6,437,317 B1 | 8/2002 | Focke et al. | |
| 2003/0172719 A1* | 9/2003 | Zentani et al. | 73/38 |
| 2003/0224918 A1* | 12/2003 | Lanier et al. | 493/39 |

(Continued)

FOREIGN PATENT DOCUMENTS

| | | |
|---|---|---|
| JP | 8-210826 A | 8/1996 |
| JP | 2000-350569 A | 12/2000 |

(Continued)

OTHER PUBLICATIONS

EPO Extended Search Report issued in corresponding EP application No. 10848377.7 on Sep. 26, 2016 (in English).

*Primary Examiner* — On S Mung
(74) *Attorney, Agent, or Firm* — Birch, Stewart, Kolasch & Birch, LLP

(57) ABSTRACT

An approximate circle approximated to the profile of a filter end face in an inspection image obtained by photographing the filter end face of a filter cigarette is obtained, and the center position of the approximate circle is found. An area indicating a string-like flavor containing element embedded in the filter is detected in the inspection image, and the position of gravity center of the area is found. Distance between the gravity center position indicating the flavor containing element and the center position of the approximate circle is determined, and thus, the quality of the flavor containing element embedded in the filter is inspected.

13 Claims, 4 Drawing Sheets

(56) References Cited

U.S. PATENT DOCUMENTS

| | | | |
|---|---|---|---|
| 2004/0173226 A1* | 9/2004 | Hanaoka et al. | 131/280 |
| 2004/0252294 A1* | 12/2004 | Hathaway | 356/237.2 |
| 2005/0255978 A1* | 11/2005 | Lanier et al. | 493/39 |
| 2006/0037619 A1* | 2/2006 | Ishikawa et al. | 131/280 |
| 2006/0050267 A1* | 3/2006 | Murakami et al. | 356/237.2 |
| 2006/0098214 A1* | 5/2006 | Wilson | A24C 5/3412 356/634 |
| 2010/0059074 A1 | 3/2010 | Brantley et al. | |
| 2010/0152008 A1 | 6/2010 | Lanier, Jr. et al. | |

FOREIGN PATENT DOCUMENTS

| | | | |
|---|---|---|---|
| JP | 2001-292757 A | | 10/2001 |
| JP | 2001292757 A | * | 10/2001 |
| JP | 2005-521399 A | | 7/2005 |
| WO | WO 03/082558 A1 | | 10/2003 |

* cited by examiner

FILTER INSPECTION METHOD AND APPARATUS

This application is a Continuation of PCT Application No. PCT/JP2010/055100 filed on Mar. 24, 2010. The entire contents are hereby incorporated by reference into the present application.

TECHNICAL FIELD

The present invention relates to a filter inspection method and apparatus suitable for inspecting quality of a string-like flavor containing element that is embedded in a columnar filter attached to a cigarette end along an axis of the filter.

BACKGROUND ART

A well-known inspection apparatus for filter cigarettes analyzes the color components of an inspection image obtained by photographing the end face of a filter and determines the presence or absence of dust or dirt adhered to the filter end face (see Patent Document 1, for example).

It has also been proposed, instead of adding a flavor component to tobacco leaves, to embed a string-like flavor containing element 3 in a columnar filter 2 attached to one end of a cigarette 1 as shown in FIG. 4 (see Patent Document 2, for example). The flavor containing element 3 of this type includes a string (thread) made of fiber which is called an aroma-chemical preserving composite fiber and having a diameter of about 1 mm, and a flavor component, such as peppermint and menthol, contained in the string. The string-like flavor containing element 3 is embedded, for example, along the axis of the filter 2.

PRIOR ART DOCUMENT

Patent Document

Patent Document 1: Unexamined Japanese Patent Publication No. 2001-292757
Patent Document 2: Unexamined Japanese Patent Publication No. 2005-521399

SUMMARY OF THE INVENTION

Concerning a filter cigarette in which the filter 2 having the embedded flavor containing element 3 is attached to one end of a cigarette, it is preferable that inspection be conducted also on the quality of the flavor containing element 3 embedded in the filter 2. More specifically, it is preferable to determine not only abnormality of the filter 2 but also whether or not the flavor containing element 3 is embedded in the filter 2, and furthermore, whether or not an embedded location of the flavor containing element 3 in the filter 2 is appropriate.

The present invention has been made in light of the above matters. It is an object of the present invention to provide a filter inspection method and apparatus capable of inspecting quality of a filter in which a flavor containing element is embedded, and especially, the quality relating to the flavor containing element with accuracy.

To determine quality of a flavor containing element embedded in a columnar filter attached to a cigarette end along an axis of the filter, a filter inspection method of the present invention finds a center position of a filter end face on an inspection image obtained by photographing the filter end face of the filter cigarette, detects an area of the flavor containing element in the filter end face on the inspection image, determines distance between the element area and the center position of the filter end face, and thus determines the quality of the filter.

Preferably, the center position of the filter end face on the inspection image is found by obtaining an approximate circle approximated to a profile of the filter end face, and a center position of the approximate circle is found as the center position of the filter end face on the inspection image. The determination of distance between the element area and the center position of the filter end face is made by finding a position of gravity center of the element area and determining distance between the position of gravity center of the element area and the center position of the filter end face.

The flavor containing element is embedded in the axis of, for example, the columnar filter. The inspection image is obtained by photographing the filter end face of a cigarette in synchronization with a transportation timing of the cigarette by using a camera situated in a lateral side of a cigarette transporting path.

The approximate circle approximated to the profile of the filter end face is obtained, for example, by finding the filter end face area on the inspection image through pattern matching between a preset reference image of the filter end face and the inspection image. A circle with preset diameter in this filter end face area is appropriated as the approximate circle.

Preferably, the element area is obtained, for example, as an area having a different color component from the filter in the filter end face. Preferably, the determination of the quality of the filter is made only on the filter whose circularity determined by comparing the approximate circle approximated to the profile of the filter end face with an outline of the filter end face meets a preset criterion.

A filter inspection apparatus of the present invention has a camera adapted to photograph a filter end face of a cigarette, a filter location detecting device adapted to find a center position of the filter end face on an inspection image photographed by the camera, an element location detecting device adapted to detect an area of the flavor containing element in the filter end face on the inspection image, and a determination device adapted to determine distance between the area of the flavor containing element and the center position of the filter end face, which are detected by the location detecting devices, and thus determines the quality of the filter.

The camera is situated in a lateral side of the cigarette transporting path and photographs the filter end face of the cigarette in synchronization with the transportation timing of the cigarette. Preferably, for example, the filter location detecting device finds a filter end face area on the inspection image by the pattern matching between a preset reference image of the filter end face and the inspection image, obtains the circle with a preset diameter in the filter end face area as an approximate circle approximated to a profile of the filter end face, and then finds a center position of the approximate circle.

Preferably, the element location detecting device obtains, as the area of the flavor containing element, an area having a different color component from the filter in the filter end face of the inspection image, and thus finds a position of gravity center of the area. Preferably, the filter inspection device has a filter-shape determination device adapted to determine a circularity of the filter by comparing the approximate circle approximated to the profile of the filter end face with an outline of the filter end face.

BEST MODE FOR CARRYING OUT THE INVENTION

A filter inspection method and apparatus according to one embodiment of the present invention will be described below with reference to the attached drawings.

Figure 1:
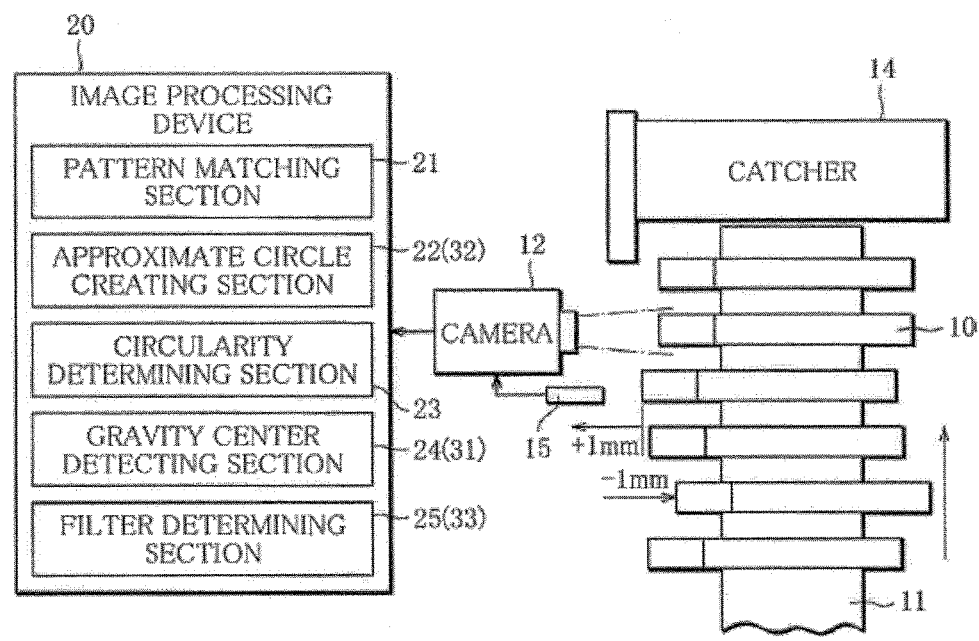
FIG. 1 is a schematic configuration view of a filter inspection apparatus according to one embodiment of the present invention.

The filter inspection apparatus of the present invention is installed in a cigarette making machine and used for online inspection on filter end faces of filter cigarettes 10. The filter inspection apparatus, the configuration of which is schematically shown in FIG. 1, comprises, as main parts, a camera 12 for photographing the filter end faces of the filter cigarettes 10 each transported in a state held onto a circumferential face of a transporting drum 11 with the filter end faces facing in the same direction, and an image processor 20 for analyzing inspection images photographed by the camera 12 and inspecting the quality of the filters. As mentioned later, the image processing device 20 includes a pattern matching section 21, an approximate circle creating section 22, a circularity determining section 23, a gravity center detecting section 24 and a filter determining section 25. The image processing device 20 has, for example, of a microcomputer in which the above functions are installed as software.

Referring to FIG. 1, reference numeral 14 represents a catcher for receiving the filter cigarette 10 transported by the transporting drum 11 and delivering the received filer cigarette 10 to a next process. Reference numeral 15 represents a trigger sensor using, for example, a photoelectric sensor, which detects the filter cigarette 10 transported in the state held onto the circumferential face of the transporting drum 11 and activates the camera 12. Although not shown, disposed in the vicinity of the camera 12 is an illumination light source that illuminates the filter end face of the cigarette 10 transported in the state held onto the circumferential face of the transporting drum 11.

Figure 2:
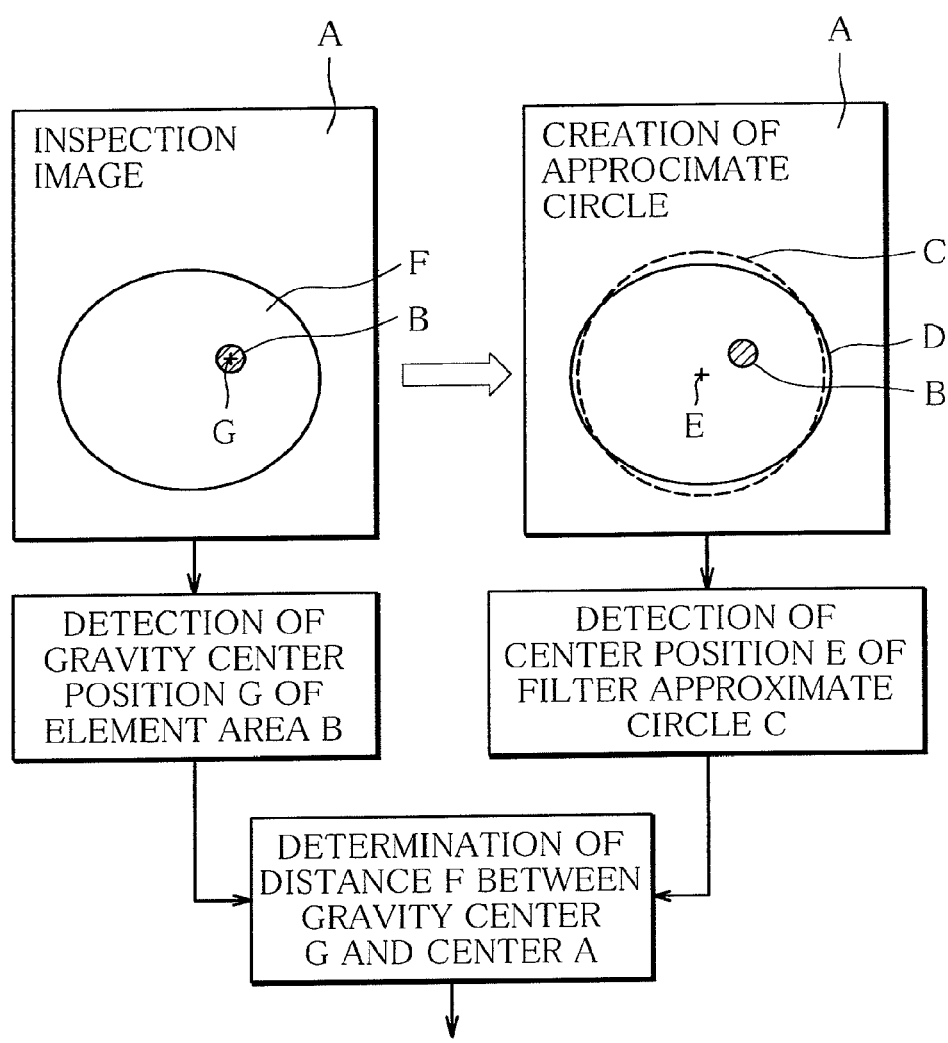
FIG. 2 shows a concept of processing of a filter inspection method according to the one embodiment of the present invention.

The inspection image obtained by photographing the filter end face of the cigarette 10 by means of the camera 12 is captured into the image processing device 20 and is offered to inspect the filter. Roughly speaking, as shown in FIG. 2, the image processing device 20 detects a filter area F in an inspection image A and also detects an area of the flavor containing element 3 in the filter area F, thereby carrying out the filter inspection method of the present invention.

More specifically, the image processing device 20 includes an element location detecting section 31 for detecting an area having a preset color component (green, for example), which differs from a color component (usually white) of the filter 2 in the filter area F, as an area B of the string-like flavor containing element 3 embedded in the filter 2, and finding a gravity center position G of the area B on the inspection image A.

The image processing device 20 further includes a filter location detecting section 32, based upon a profile D of the filter area F, the profile D showing the shape of the filter end face, for obtains an approximate circle C approximated to the profile D, and finding a center position E of the approximate circle C in the inspection image A. The image processing device 20 further includes a filter determination section 33 for finding distance F between the gravity center position G of the element area B, which is obtained by the element location detecting section 31, and the center position E of the approximate circle C, which is obtained by the filter location detecting section 32, comparing the distance F with a preset threshold value and determining whether the flavor containing element 3 is embedded in an axis of the filter 2.

The threshold value indicates an acceptable limit allowing the flavor containing element 3 to deviate from the axis of the filter 2 and is set at about 0.9 mm, for example. When the distance F between the gravity center position G of the element area B and the center position E of the approximate circle C is more than the threshold value, the filter determination section 33 determines that the flavor containing element 3 is abnormal (defective) and issues a command to eliminate a cigarette 10 attached with the filter 2.

In other words, the cigarette inspection method of the present invention obtains the profile D showing the shape of the filter end face from the inspection image A of the filter end face, and then finds the center position of the profile D. More specifically, a coordinate of the center position E of the approximate circle C on the inspection image A, the circle being approximated to the profile D of the filter end face, is obtained as the center position of the filter end face. At the same time, the element area B in the filter area F is also detected and obtained as an embedded location of the flavor containing element 3. To be specific, the gravity center position G of the element area B is detected as the embedded location of the flavor containing element 3 in the filter 2. Difference between a coordinate of the gravity center position G on the inspection image A and the coordinate of the center position E of the filter 2 is treated as a deviation amount of the flavor containing element 3 from the axis of the filter 2. A determination is made as to whether or not the deviation amount is in an acceptable range.

According to the cigarette inspection method of the present invention, it is effectively determined whether the flavor containing element 3 is embedded properly (accurately) at the axis of the filter 2, regardless of distortion of the filter 2 in the cigarette 10. Furthermore, since the determination of quality of the filter can be made by the simple image processing, the burden of processing which applied to the image processing device 20 is not so severe. The cigarette inspection method of the present invention is suitable for conducting the real-time filter inspection of the filter cigarette 10 transported in the state held onto the circumferential face of the transporting drum 11.

Figure 3:
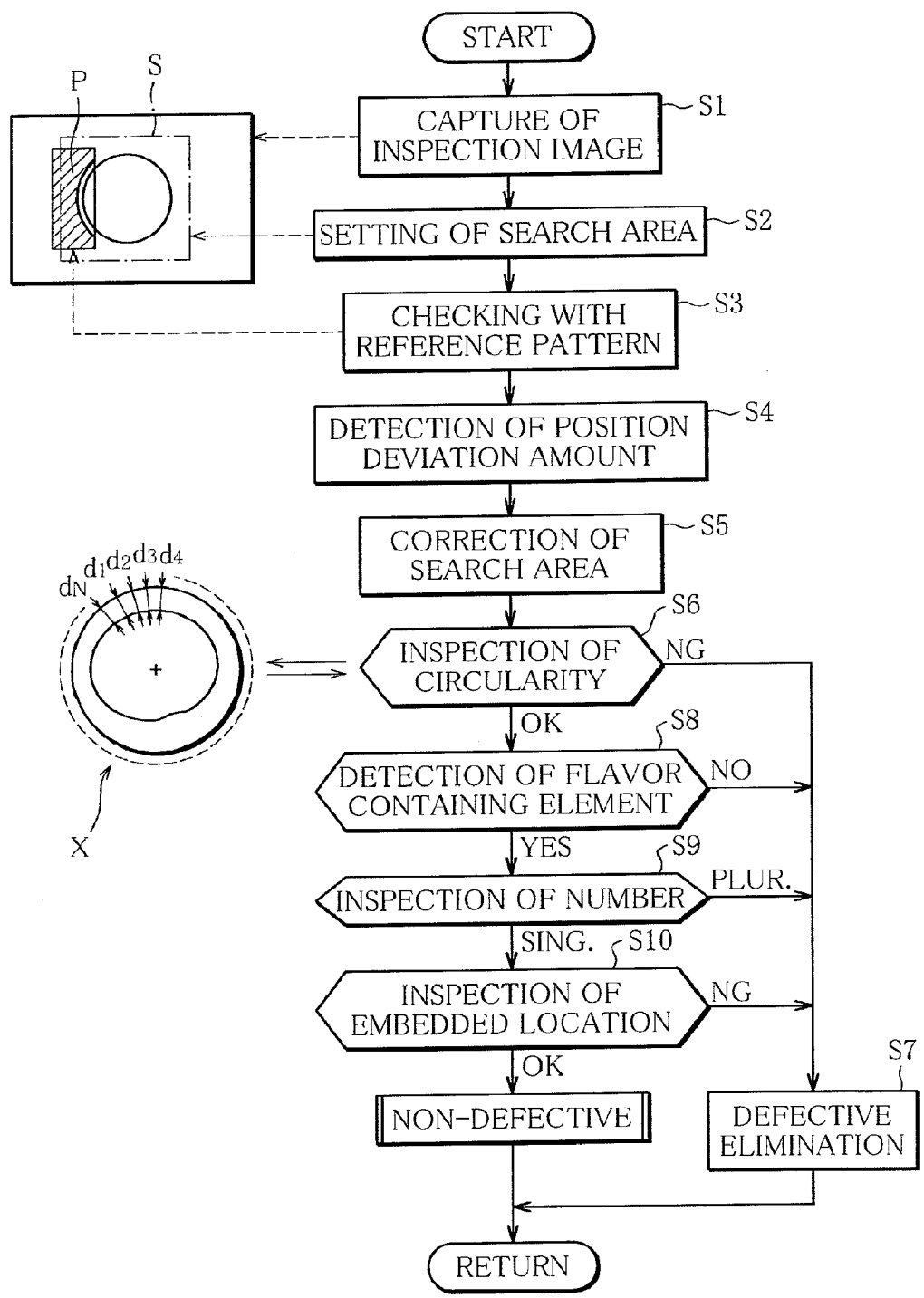
FIG. 3 shows an example of processing routine of filter inspection using the filter inspection method of the present invention.
Figure 4:
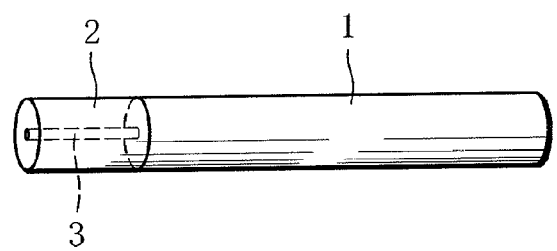
FIG. 4 is a schematic view of a filter cigarette in which a filter including an embedded string-like flavor containing element is attached to one end of a cigarette.

FIG. 3 shows the entire processing routine of the filter inspection including the inspection of the flavor containing element 3 in the filter 2 by using the filter inspection apparatus of the present invention. The filter inspection is started by photographing the filter end face of the cigarette 10 to be inspected by means of the camera 12 and capturing the image thereof into the image processing device 20 <Step S1>. A search area S to be used as an object of image processing is tentatively determined on the captured image <Step S2>.

For example, a partial image previously obtained by cutting out a part of the filter end face in the search area S to have an arc-like shape is used as a reference pattern P, and a position where the reference pattern P coincides with an image pattern F of the filter end face in the captured image is searched <Step S3>. This processing is conducted in the pattern matching section 21 installed in the image processing device 20. The position where the reference pattern P coincides with the image pattern F of the filter end face is obtained as information for extracting an area including the entire filter end face as an inspection image A.

Deviation between a preset reference position of the reference pattern P on the captured image and the position where the reference pattern P and the image pattern of the filter end face coincide with each other is detected as a deviation amount of the image F of the filter end face in the captured image <Step S4>. Based upon the deviation amount, the search area S in the captured image, which is the object of the image processing, is corrected <Step S5>. This deviation correction is made in consideration that the deviation is prone to occur in the image of the filter end face in the captured image even if the filter cigarettes 10 are continuously transported in the state held onto the transporting drum 11 are detected by using the trigger sensor 15, and the filter end faces of the cigarettes 10 are photographed in synchronization with the detection timing thereof.

After the search area S with regard to the captured image is set as stated, and thus, the area to be processed for the filter inspection by the image processing device 20 is set as an inspection image, the approximate circle creating section 22 included in the image processing device 20 is operated. The approximate circle creating section 22 forms a part of the filter location detecting section 32 and functions to obtain the profile D of the filter area F, which shows the shape of the filter end face on the inspection image A (search area S) and, based upon the profile D, obtain the approximate circle C approximated to the profile D.

If the approximate circle C approximated to the filter end face on the inspection image A is thus obtained, the coordinate of the center position of the approximate circle C on the inspection image A is unambiguously defined by information (function) that identifies the approximate circle C. The approximate circle creating section 22 obtains the coordinate of the center position of the approximate circle C as a center position of the filter end face, in spite of the distortion of the filter 2 (distortion of the profile of the filter end face).

The image processing device 20 then operates the circularity determining section 23, and compares the approximate circle C obtained as described above with the profile shape of the filter 2 on the inspection image A, to thereby inspect the circularity (roundness) of the profile shape of the filter 2 <Step S6>. The circularity inspection includes concept of processing as shown by a schematic depiction X in FIG. 3, for example. The circularity inspection obtains distances d1, d2, ..., between the approximate circle C and the profile of the filter 2 in a radial direction of the approximate circle C at a plurality of inspection points (about 100 points, for example) that equally divide the approximate circle C. For example, the circularity inspection determines that the roundness of the filter 2 is not maintained, or that the filter 2 is distorted, when at least one of the distances d1, d2, ..., is larger than a predetermined threshold value.

When it is considered that the profile of the filter 2 exists on the approximate circle C, for example, by 95 percent or more of the inspection points, that is, when the profile shape of the filter end face is virtually the same as the approximate circle C, it is possible to determine that the circularity of the filter end face, which ensures the quality of the filter cigarette, is retained.

If the circularity of the filter 2 is not maintained, a command to eliminate the cigarette attached with the filter 2 as "filter defectiveness" is delivered <Step S7>, and the subsequent filter inspection is not conducted. Only if the filter cigarette 10 passes the circularity inspection, the filter cigarette 10 undergoes the inspection processing with respect to the flavor containing element 3 embedded in the filter 2 thereof.

The inspection processing with respect to the flavor containing element 3 embedded in the filter 2 is started by causing the element location detecting section 31 to operate and detecting the area B having the color component of the flavor containing element 3 in the image area F of the filter end face <Step S8>. If the detection processing fails to detect the area B of the flavor containing element 3, it is determined that the flavor containing element 3 is not normally embedded in the filter 2, or that the filter 2 is a defective. In this case, the command to eliminate the cigarette attached with the filter 2 as "filter defectiveness" is also delivered <Step S7>, and the subsequent filter inspection is not conducted.

If the area B of the flavor containing element 3 is detected, the number of detected areas B is determined <Step S9>. In case where the inspection object is the filter 2 in which only one string-like flavor containing element 3 is embedded in the axis thereof, unless only one area B is detected, that is, if there is more than one area B detected, it is determined that the filter 2 is a defective or that a foreign matter other than the flavor containing element 3 is contained in the filter 2. In this case, the command to eliminate the cigarette attached with the filter 2 as "filter defectiveness" is also delivered <Step S7>, and the subsequent filter inspection is not conducted.

When only one area B of the flavor containing element 3 is detected, the gravity-center detecting section 24 forming the element location detecting section 31 is operated, and the coordinate of the gravity center position of the area B on the inspection image A is obtained. The distance F between the obtained coordinate of the gravity center position of the area B and the coordinate of the center position of the approximate circle C is obtained by the filter determining section 25 serving as the filter determination section 33. A determination is then made as to whether the distance F is equal to or less than the predetermined threshold value (0.9 mm, for example). In other words, it is determined whether the embedded position of the flavor containing element 3, which is indicated as the gravity center of the area B, is located in the axis of the filter 2, which is indicated as the center position of the approximate circle C, within a predetermined allowable error range <Step S10>.

If it is detected by the foregoing detection that the embedded position of the flavor containing element 3 (gravity center position of the area B) is deviated to a great degree from the axis of the filter 2 (center of the approximate circle C), this is determined as "filter defectiveness". The command to eliminate the cigarette attached with the filter 2 is delivered <Step S7>.

If the embedded position of the flavor containing element 3 (gravity center position of the area B) is located in the axis of the filter 2 (center of the approximate circle C) within the allowable error range, it is determined that the filter 2 is normal (non-defective) <Step S10>. Only if it is confirmed that the flavor containing element 3 is embedded in the axis of the filter 2, it is determined that the filter cigarette 10 in which the filter 2 is attached to one end of the cigarette 1 is normal (non-defective).

As described, the cigarette inspection method and apparatus for inspecting the flavor containing element 3 embedded in the filter 2 in the filter cigarette 10 appreciates the shape of the filter 2 on the inspection image of the filter end face as the approximate circle C that is approximated to an outer edge thereof, and also appreciates the embedded location of the flavor containing element 3 embedded in the filter 2 as the gravity center position of the element area B. Consequently, the cigarette inspection method and apparatus can easily and accurately determine the embedded location of the flavor containing element 3 in the filter 2. Furthermore, the cigarette inspection method and apparatus can determine the embedded location of the flavor containing element 3, regardless of some distortion in the filter 2. Even if the filter cigarette 10 transported in the state held onto the transporting drum 11 is shifted in some degree in the axial direction thereof, since the shape of the filter is appreciated as the approximate circle C, the filter inspection can be conducted with no effects of the axial shift of the filter cigarette 10. This sufficiently increases determination accuracy.

Since the embedded location of the flavor containing element 3 is determined after the determination of the circularity (roundness) of the filter 2, the determination of the number of detected areas B as the flavor containing element 3, and the elimination of the abnormal filter 2 (defective), the present invention has the advantage that the abnormality of the filter 2 is efficiently determined at the same time.

The present invention is not limited to the foregoing embodiment. The present invention has been described with reference to the inspection of the filter 2 in which one string-like flavor containing element 3 is embedded in the axis thereof. However, the inspection can be conducted in the same manner on a filter including a plurality of string-like flavor containing elements 3 embedded in parallel with the axis of the filter 2 at equiangular intervals and apart from the axis of the filter 2 by same distance. In this case, a determination is made not only as to whether areas B being indicative of the respective string-like flavor containing elements 3 are at the same distance from the center of the approximate circle C but also, for example, as to whether the intervals between the areas B are equal to each other. This way, it can be determined whether the string-like flavor containing elements 3 are embedded at equiangular intervals.

Although the present invention focuses on the color component of the flavor containing element 3 and detects the area B in the filter end face, in which the flavor containing element 3 exists, it is also possible to detect an area having a color component other than the color component of the filter 2 and determine the size and shape of the area, to thereby distinguish the flavor containing element 3 from dust or dirt adhered to the filter end face and thus detect only the area B where the flavor containing element 3 exists. The present invention may be modified in various ways without deviating from the gist thereof.

EXPLANATION OF REFERENCE SIGNS

1 Cigarette
2 Filter
3 String-like flavor containing element
10 Filter cigarette
12 Camera
20 Image processing device
21 Pattern matching section
22 Approximate circle creating section
23 Circularity determining section
24 Gravity center detecting section
25 Filter determining section
31 Element location detecting section
32 Filter location detecting section
33 Filter determination section
A Inspection image
B Element area
C Approximate circle approximated to a filter profile

The invention claimed is:

1. A filter inspection method for inspecting quality of a columnar filter attached to a cigarette end, the filter having a flavor containing element embedded in the filter along an axis of the filter so as to be placed at a preset location with respect to a center position of a filter end face of the filter, the method comprising steps of:
    finding the center position of the filter end face on an inspection image obtained by photographing the filter end face, based on a profile of the filter end face on the inspection image;
    detecting an area of the flavor containing element in the filter end face on the inspection image;
    obtaining distance between the element area and the center position of the filter end face along a radial direction of the filter end face; and
    determining the quality of the filter, based on the distance.

2. The filter inspection method according to claim 1, wherein the center position of the filter end face on the inspection image is found as a center position of an approximate circle approximated to a profile of the filter end face after the approximate circle is obtained.

3. The filter inspection method according to claim 1, wherein the determination of distance between the element area and the center position of the filter end face is made by finding a position of gravity center of the element area and determining distance between the position of gravity center of the element area and the center position of the filter end face.

4. The filter inspection method according to claim 1, wherein the flavor containing element is embedded in the axis of the columnar filter.

5. The filter inspection method according to claim 1, wherein the inspection image is obtained by photographing the filter end face of the cigarette in synchronization with a transportation timing of the cigarette by using a camera situated in a lateral side of a cigarette transporting path.

6. The filter inspection method according to claim 2, wherein the approximate circle approximated to the profile of the filter end face is obtained as a circle of a filter end face is on the inspection image, the circle having a preset diameter,
    wherein the filter end face area is found by pattern matching between a preset reference image of the filter end face and the inspection image.

7. The filter inspection method according to claim 1, wherein the element area is obtained as an area having a different color component from the filter in the filter end face.

8. The filter inspection method according to claim 1, wherein determination of the quality of the filter is made only on the filter whose circularity determined by comparing the approximate circle approximated to the profile of the filter end face with an outline of the filter end face meets a preset criterion.

9. A filter inspection apparatus for inspecting quality of a columnar filter attached to a cigarette end, the filter having a flavor containing element embedded in the filter along an axis of the filter so as to be placed at a preset location with respect to a center position of the filter end face of the filter, the apparatus comprising:
- a camera adapted to photograph the filter end face of the cigarette;
- a filter location detecting device adapted to find the center position of the filter end face in an inspection image photographed by said camera, based on a profile of the filter end face on the inspection image;
- an element location detecting device adapted to detect an area of the flavor containing element in the filter end face on the inspection image;
- an obtaining device adapted to obtain distance between the area of the flavor containing element and the center position of the filter end face along a radial direction of the filter end face, which are detected by said detecting devices; and
- a determination device adapted to determine the quality of the filter, based on the distance.

10. The filter inspection apparatus according to claim 9, wherein said camera is situated in a lateral side of a cigarette transporting path and photographs the filter end face of the cigarette in synchronization with the transportation timing of the cigarette.

11. The filter inspection apparatus according to claim 9, wherein said filter location detecting device finds a filter end face area on the inspection image by pattern matching between a preset reference image of the filter end face and the inspection image, obtains the circle with a preset diameter in the filter end face area as an approximate circle approximated to a profile of the filter end face, and then finds a center position of the approximate circle.

12. The filter inspection apparatus according to claim 9, wherein said element location detecting device obtains, as the area of the flavor containing element, an area having a different color component from the filter in the filter end face of the inspection image, and thus finds a position of gravity center of the area.

13. The filter inspection apparatus according to claim 9, further comprising: a filter-shape determination device adapted to determine circularity of the filter by comparing the approximate circle approximated to the profile of the filter end face with an outline of the filter end face.

* * * * *